US010207115B2

(12) United States Patent
Echt et al.

(10) Patent No.: US 10,207,115 B2
(45) Date of Patent: Feb. 19, 2019

(54) METHOD AND SYSTEMS FOR HEART FAILURE PREVENTION AND TREATMENTS USING ULTRASOUND AND LEADLESS IMPLANTABLE DEVICES

(71) Applicant: EBR Systems, Inc., Sunnyvale, CA (US)

(72) Inventors: Debra S. Echt, Tiburon, CA (US); Richard E. Riley, Palo Alto, CA (US); Mark W. Cowan, San Jose, CA (US); Axel F. Brisken, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 15/138,582

(22) Filed: Apr. 26, 2016

(65) Prior Publication Data
US 2016/0235976 A1 Aug. 18, 2016

Related U.S. Application Data

(62) Division of application No. 12/829,183, filed on Jul. 1, 2010, now Pat. No. 9,333,364, which is a division
(Continued)

(51) Int. Cl.
*A61N 1/36* (2006.01)
*A61N 1/362* (2006.01)
(Continued)

(52) U.S. Cl.
CPC .......... *A61N 1/362* (2013.01); *A61N 1/3627* (2013.01); *A61N 1/3787* (2013.01); *A61N 7/00* (2013.01);
(Continued)

(58) Field of Classification Search
CPC .. A61N 1/362; A61N 1/3627; A61N 1/37205; A61N 1/3787; A61N 2007/0004; A61N 7/00
See application file for complete search history.

(56) References Cited

U.S. PATENT DOCUMENTS 3,659,615 A 5/1972 Carl
3,693,627 A 9/1972 Barouh
(Continued)

FOREIGN PATENT DOCUMENTS

DE 4330680 A1 3/1995
EP 0112082 A2 6/1984
(Continued)

OTHER PUBLICATIONS

Abraham et al., for the Miracle study group, "Cardiac Resynchronization in Chronic Heart Failure," N Engl J Med, 2002;346:1845-53.
(Continued)

*Primary Examiner* — Amanda Hulbert
(74) *Attorney, Agent, or Firm* — Perkins Coie LLP

(57) ABSTRACT

The present invention relies on a controller-transmitter device to deliver ultrasound energy into cardiac tissue in order to directly improve cardiac function and/or to energize one or more implanted receiver-stimulator devices that transduce the ultrasound energy to electrical energy to perform excitatory and/or non-excitatory treatments for heart failure. The acoustic energy can be applied as a single burst or as multiple bursts.

6 Claims, 4 Drawing Sheets

Related U.S. Application Data of application No. 11/468,002, filed on Aug. 29, 2006, now Pat. No. 7,765,001.

(60) Provisional application No. 60/713,241, filed on Aug. 31, 2005.

(51) Int. Cl.
*A61N 1/378* (2006.01)
*A61N 7/00* (2006.01)
*A61N 1/372* (2006.01)

(52) U.S. Cl.
CPC .. *A61N 1/37205* (2013.01); *A61N 2007/0004* (2013.01)

(56) References Cited

U.S. PATENT DOCUMENTS

| | | | |
|---|---|---|---|
| 3,698,398 A | 10/1972 | Barouh | |
| 3,735,756 A | 5/1973 | Richards et al. | |
| 3,832,994 A | 9/1974 | Bicher et al. | |
| 3,857,382 A | 12/1974 | Williams et al. | |
| 3,939,844 A | 2/1976 | Pequignot | |
| 3,942,534 A | 3/1976 | Allen et al. | |
| 4,181,133 A | 1/1980 | Kolenik et al. | |
| 4,256,115 A | 3/1981 | Bilitch | |
| 4,265,228 A | 5/1981 | Zoll | |
| 4,280,502 A | 7/1981 | Baker, Jr. et al. | |
| 4,372,296 A | 2/1983 | Fahim | |
| 4,561,442 A | 12/1985 | Vollmann et al. | |
| 4,577,633 A | 3/1986 | Berkovits et al. | |
| 4,651,716 A | 3/1987 | Forester et al. | |
| 4,690,144 A | 9/1987 | Rise et al. | |
| 4,830,006 A | 5/1989 | Haluska et al. | |
| 5,018,523 A | 5/1991 | Bach, Jr. et al. | |
| 5,063,928 A | 11/1991 | Grevis et al. | |
| 5,103,129 A | 4/1992 | Slayton et al. | |
| 5,113,859 A | 5/1992 | Funke | |
| 5,165,403 A | 11/1992 | Mehra | |
| 5,170,784 A | 12/1992 | Ramon et al. | |
| 5,174,289 A | 12/1992 | Cohen | |
| 5,193,539 A | 3/1993 | Schulman et al. | |
| 5,292,338 A | 3/1994 | Bardy | |
| 5,377,166 A | 12/1994 | Kuhn | |
| 5,405,367 A | 4/1995 | Schulman et al. | |
| 5,411,535 A | 5/1995 | Fujii et al. | |
| 5,433,731 A | 7/1995 | Hoegnelid et al. | |
| 5,598,845 A | 2/1997 | Chandraratna et al. | |
| 5,674,251 A | 10/1997 | Combs et al. | |
| 5,749,909 A | 5/1998 | Schroeppel et al. | |
| 5,751,539 A | 5/1998 | Stevenson et al. | |
| 5,757,104 A | 5/1998 | Getman et al. | |
| 5,766,227 A | 6/1998 | Nappholz et al. | |
| 5,800,464 A | 9/1998 | Kieval | |
| 5,814,089 A | 9/1998 | Stokes et al. | |
| 5,817,130 A | 10/1998 | Cox et al. | |
| 5,844,349 A | 12/1998 | Oakley et al. | |
| 5,871,506 A | 2/1999 | Mower | |
| 5,879,303 A | 3/1999 | Averkiou et al. | |
| 5,935,158 A | 8/1999 | Holmstroem et al. | |
| 5,978,204 A | 11/1999 | Stevenson | |
| 5,998,910 A | 12/1999 | Park et al. | |
| 6,037,704 A | 3/2000 | Welle | |
| 6,070,101 A | 5/2000 | Struble et al. | |
| 6,078,837 A | 6/2000 | Peterson et al. | |
| 6,110,098 A | 8/2000 | Renirie et al. | |
| 6,141,588 A | 10/2000 | Cox et al. | |
| 6,223,079 B1 | 4/2001 | Bakels et al. | |
| 6,233,484 B1 | 5/2001 | Ben-Haim et al. | |
| 6,236,887 B1 | 5/2001 | Ben-Haim et al. | |
| 6,285,906 B1 | 9/2001 | Ben-Haim et al. | |
| 6,298,268 B1 | 10/2001 | Ben-Haim et al. | |
| 6,298,269 B1 | 10/2001 | Sweeney | |
| 6,317,631 B1 | 11/2001 | Ben-Haim et al. | |
| 6,330,475 B1 | 12/2001 | Renirie et al. | |
| 6,330,476 B1 | 12/2001 | Ben-Haim et al. | |
| 6,363,279 B1 | 3/2002 | Ben-Haim et al. | |
| 6,366,816 B1 | 4/2002 | Marchesi | |
| 6,408,205 B1 | 6/2002 | Renirie et al. | |
| 6,424,234 B1 | 7/2002 | Stevenson | |
| 6,439,236 B1 | 8/2002 | Porter et al. | |
| 6,442,424 B1 | 8/2002 | Ben-Haim et al. | |
| 6,445,953 B1 | 9/2002 | Bulkes et al. | |
| 6,463,324 B1 | 10/2002 | Ben-Haim et al. | |
| 6,464,680 B1 | 10/2002 | Brisken et al. | |
| 6,522,926 B1 | 2/2003 | Kieval et al. | |
| 6,527,729 B1 | 3/2003 | Turcott | |
| 6,534,895 B2 | 3/2003 | Kadota et al. | |
| RE38,119 E | 5/2003 | Mower | |
| 6,575,956 B1 | 6/2003 | Brisken et al. | |
| 6,628,989 B1 | 9/2003 | Penner et al. | |
| 6,645,145 B1 | 11/2003 | Dreschel et al. | |
| 6,647,292 B1 | 11/2003 | Bardy et al. | |
| 6,654,638 B1 | 11/2003 | Sweeney | |
| 6,671,547 B2 | 12/2003 | Lyster et al. | |
| 6,707,230 B2 | 3/2004 | Smith et al. | |
| 6,721,597 B1 | 4/2004 | Bardy et al. | |
| 6,725,093 B1 | 4/2004 | Ben-Haim et al. | |
| 6,728,576 B2 | 4/2004 | Thompson et al. | |
| 6,754,528 B2 | 6/2004 | Bardy et al. | |
| 6,754,531 B1 | 6/2004 | Kroll et al. | |
| 6,764,446 B2 | 7/2004 | Wolinsky et al. | |
| 6,788,974 B2 | 9/2004 | Bardy et al. | |
| 6,795,732 B2 | 9/2004 | Stadler et al. | |
| 6,834,204 B2 | 12/2004 | Ostroff et al. | |
| 6,856,835 B2 | 2/2005 | Bardy et al. | |
| 6,970,742 B2 | 11/2005 | Mann et al. | |
| 7,043,292 B2 | 5/2006 | Tarjan et al. | |
| 7,130,681 B2 | 10/2006 | Gebhardt et al. | |
| 7,200,437 B1 | 4/2007 | Nabutovsky et al. | |
| 7,283,874 B2 * | 10/2007 | Penner | A61B 5/0031 607/33 |
| 7,349,740 B2 | 3/2008 | Soykan et al. | |
| 7,489,967 B2 | 2/2009 | Von et al. | |
| 7,610,092 B2 | 10/2009 | Cowan et al. | |
| 7,765,001 B2 | 7/2010 | Echt et al. | |
| 8,655,444 B2 | 2/2014 | Ben-Haim et al. | |
| 9,333,364 B2 | 5/2016 | Echt et al. | |
| 2002/0077673 A1 | 6/2002 | Penner et al. | |
| 2003/0013974 A1 | 1/2003 | Natarajan et al. | |
| 2003/0069625 A1 | 4/2003 | Ley et al. | |
| 2004/0015104 A1 | 1/2004 | Goldberger | |
| 2004/0134496 A1 | 7/2004 | Cho et al. | |
| 2004/0167580 A1 | 8/2004 | Mann et al. | |
| 2004/0172083 A1 | 9/2004 | Penner | |
| 2004/0204744 A1 | 10/2004 | Penner et al. | |
| 2004/0260346 A1 | 12/2004 | Overall et al. | |
| 2005/0070962 A1 | 3/2005 | Echt et al. | |
| 2006/0009831 A1 | 1/2006 | Lau et al. | |
| 2006/0106442 A1 | 5/2006 | Richardson et al. | |
| 2006/0135999 A1 | 6/2006 | Bodner et al. | |
| 2006/0136004 A1 | 6/2006 | Cowan et al. | |
| 2006/0136005 A1 | 6/2006 | Brisken et al. | |
| 2006/0224067 A1 | 10/2006 | Giftakis et al. | |
| 2006/0241701 A1 | 10/2006 | Markowitz et al. | |
| 2007/0027508 A1 | 2/2007 | Cowan | |
| 2007/0032749 A1 | 2/2007 | Overall et al. | |
| 2007/0088394 A1 | 4/2007 | Jacobson | |
| 2007/0088397 A1 | 4/2007 | Jacobson | |
| 2007/0088398 A1 | 4/2007 | Jacobson | |
| 2007/0150009 A1 | 6/2007 | Kveen et al. | |
| 2007/0232936 A1 | 10/2007 | Mann et al. | |
| 2007/0260286 A1 | 11/2007 | Giftakis et al. | |
| 2007/0265677 A1 | 11/2007 | Giftakis et al. | |
| 2012/0109002 A1 * | 5/2012 | Mothilal | A61B 5/0215 600/549 |

FOREIGN PATENT DOCUMENTS

| | | |
|---|---|---|
| EP | 0112082 A3 | 5/1985 |
| EP | 0617981 A1 | 10/1994 |
| WO | WO-9639079 A1 | 12/1996 |
| WO | WO-9725098 A1 | 7/1997 |
| WO | WO-9961058 A1 | 12/1999 |

(56) References Cited

FOREIGN PATENT DOCUMENTS

| WO | WO-0215768 A2 | 2/2002 |
|---|---|---|
| WO | WO-0215768 A3 | 4/2002 |
| WO | WO-03070323 A1 | 8/2003 |
| WO | WO-2007027940 A2 | 3/2007 |
| WO | WO-2007027940 A3 | 6/2007 |

OTHER PUBLICATIONS

ACC/AHA Task Force on Practice Guidelines, "Evaluation and Management of Chronic Heart Failure in the Adult," JACC 2002;38:2101-13.
Allessie et al., "Regional Control of Atrial Fibrillation by Rapid Pacing in Conscious Dogs," Circulation 1991;84:1689-97.
Ansalone et al., "Bi-ventricular Pacing I Heart Failure:Back to Basics in the Pathophysiology of Left Bundle Branch Block to Reduce the Number of Nonresponders," Am J Cardiol 2003;91:55F-61F.
Auricchio et al., "Cardiac Resynchronization Therapy: Current State of the Art," Circulation 2004;109:300-307.
Bardy, et al. The Totally Subcutaneous ICD System (The S-ICD). PACE. 2002; 24,578.
Becker et al, "Suppression of Atrial Fibrillation by Multisite and Septal Pacing in a Novel Experimental Model", Cardiovascular Research 2001;54(2):476-481.
Bradley, et al. Cardiac resynchronization and death from progressive heart failure: a meta-analysis of randomized controlled trials. JAMA. Feb. 12, 2003;289(6):730-40.
Camm, et al. Chapter 6: Nonpharmaceutical treatment of atrial fibrillation, In Atrial Fibrillation. Facts from Yesterday—Ideas for tomorrow. Futura Publishing Company, Inc., Armonk, NY, 1994, pp. 125-147.
Dalecki, et al. Effects of Pulsed Ultrasound on the Frog Heart: I. Thresholds for Changes in Cardiac Rhythm and Aortic Pressure. Ultrasound in Med. & Biol. 1993; 19:385-390.
Dalecki et al., "Effects of Pulsed Ultrasound on the Frog Heart: II. An Investigation of Heating as a Potential Mechanism," Ultrasound in Med. & Biol. 1993; 19:391-398.
Dalecki et al., "Thresholds for premature ventricular contractions in frog hearts exposed to lithotripter fields," Ultrasound in Med. & Biol. 1991; 17:341-346.
Daoud, et al. Implantation techniques and chronic lead parameters of biventricular pacing dual-chamber defibrillators. J Cardiovasc Electrophysiol. Oct. 2002;13(10):964-70.
Daubert, et al. Permanent left ventricular pacing with transvenous leads inserted into the coronary veins. Pacing Clin Electrophysiol. Jan. 1998;21(1 Pt 2):239-45.
Daubert, et al. Use of Specifically Designed Coronary Sinus Leads for Permanent Left Ventricular Pacing: Preliminary Experience. PACE, 1997; 20: II—NASPE Abstract 17, Apr. 1997.
David Trial Investigators, The Dual Chamber and WI Implantable Defibrillator (DAVID) Trial, JAMA 2002;288:3115-3123.
Deshmukh et al. "Direct His-bundle pacing: present and future," PACE 2004;27 [Pt.11]:862-70.
Doshi, et al. The left ventricular-based cardiac stimulation post AV nodal ablation evaluation (PAVE) study. Oral presentation at American college of Cardiology. Mar. 2004.
Ellenbogen et al., "Detection and Management of an Implantable Cardioverter Defibrillator Lead Failure," JACC. 2003;41:73-80.
Feldman et al, "Comparison of medical therapy, resynchronization and defibrillation therapies in heart failure trial (COMPANION)," Presented at ACC 2003 Late Breaking Clinical Trials, 1 page.
Forester, et al. Enhancement of contractility in rat isolated papillary muscle with therapeutic ultrasound. MoL Cell Cardiol. 1982; 14(8):475-7.
Forester. et al. Ultrasound Intensity and Contractile Characteristics of Rat Isolated Papillary Muscle. Ultrasound in Med. And Biol. 1985;11(4):591-598.

Franz, "Mechano-electrical feedback in ventricular myocardium," Cardiovascular Research. 1996; 32:15-24.
Gregoratos, et al. ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation. 2002; 106:2145-2161.
Hu et al., "Stretch-Activated Ion Channels in the Heart," J. Mot. Cell Cardiol. 1997; 29:1511-1523.
International preliminary report on patentability dated Mar. 4, 2008 for PCT/US2006/034102.
International search report and written opinion dated May 8, 2007 for PCT/US2006/034102.
Johnson et al., "Adaptive Pacing During Ventricular Fibrillation," PACE 2003;26:1824-36.
Kalman J.M. et al, "Regional Entrainment of Atrial Fibrillation in Man", J Cardiovasc Electrophysiol 1991;7:867-76.
Kass et al., "Improved Left Ventricular Mechanics from Acute VDD Pacing in Patients with Dilated Cardiomyopathy and Ventricular Conduction Delay," Circulation 1999;99:1567-73.
Kenknight, et al. Regional Capture of Fibrillating Ventricular Myocardium. Circ Res 1999;77:849-55.retrieve from the Internet: circres.ahajournals.org/cgi/content/full/77/4/849.
Kohl et al., Stretch-Induced Changes in Heart Rate and Rhythm: Clinical Observations, Experiments and Mathematical Models. Progress in Biophysics & Molecular Biology, 1999; 71:91-138.
Kohl et al., "Sudden Cardiac Death by Commotio Cordis: Role of Mechano-Electrical Feedback," Cardiovascular Research, 2001; 50:280-289.
Leclercq, et al. Is Dual Site Better than Single Site Atrial Pacing in the Prevention of Atrial Fibrillation? PACE 2000;23:2102-7.
Leclercq et al., "Systolic Improvement and Mechanical Resynchronization does not Require Electrical Synchrony in the Dilated Failing Heart with Left Bundle-Branch Block", Circulation 2002;106:1760-1763.
Leclerq, et al. Acute Hemodynamic Effects of Biventricular DDD Pacing in Patients with End-Stage Heart Failure. JACC 1998;32:1825-1831.
Lee et al., "Effect of implantable Defibrillators of Arrhythmic Events and Mortality in the Multicenter Unsustained Tachycardia Trial," Circulation. 2002; 106:233-238.
Linde et al., "Long-Term Benefits of Biventricular Pacing in Congestive Heart Failure: From the Multisite Stimulation in Cardiomyopathy (MUSTIC) Study", J Am Coll Cardiol 2002;40:111-118.
Marrouche, et al. Nonexcitatory stimulus delivery improves left ventricular function in hearts with left bundle branch block. J Carcovasc Electrophysiol. 2002; 13(7):691-695.
McPherson, et al. Seizing the Science of Ultrasound Beyond Imaging and Into Physiology and Therapeutics. Journal of the American College of Cardiology 2003;41:1628-30.
Meltzer, et al. Therapeutic Cardiac Ultrasound. American Journal of Cardiology. 1991;67:422-4.
Miracle Trial Investigators, "Combined Cardiac Resynchronization and Implantable Cardioversion Defibrillation in Advanced Heart Failure: the Miracle ICD Trial," JAMA 2003;289:2685-2694.
Mirza et al, "Biatrial Pacing for Paroxysmal Atrial Fibrillation", J Am Coll Cardiol 2002;40:457-463.
Miyamoto, et al. Coronary Vasodilation by Noninvasive Transcutaneous Ultrasound An In ivo Canine Study. Journal of the American College of Cardiology. 2003;41:1623-7.
Mohri, et al. Cardiac Contractility Modulation by electric Currents Applied During the Refractory Period. Am J Physiol Heart Ciro Physiol. 2002;282:H1642-1647.
Mond. Selective Site Pacing: The Future of Cardiac Pacing? PACE 2004;27:835-836.
Mortimer, et al. Letter to the Editor: Altered Myocardial Contractility with Pulsed Ultrasound. Ultrasound in Med and Biol. 1987;13(9):L567-9.
Moss et al., "Prophylactic Implantation of a Defibrillator in Patients with Myocardial Infarction and Reduced Ejection Fraction," N Engl J Med. 2002; 346:877-933.

(56) References Cited

OTHER PUBLICATIONS

Niehaus et al., "Non-Contact Cardiac Stimulation with locused Ultrasound Pulses," PACE 2003: 26:1023.
Nielsen et al., "A Randomized Comparison of Atrial and Dual-Chambered Pacing in 177 Consecutive Patients With Sick Sinus Syndrome," J Am Coll Cardiol 2003;42:614-623.
Nishida, et al. Extracorporeal cardiac shock wave therapy markedly ameliorates ischemia-induced myocardial dysfunction in pigs in vivo. Circulation. 2004;110:3055-3061.
Nolte, et al. Mechanically Induced Ventricular Extrasystoles in the Isolated Perfused Guinea-Pig Heart. Arzneim.-Forsch/Drug Research. 1987; 37(11): 1025-1029.
Notice of allowance dated Jan. 11, 2016 for U.S. Appl. No. 12/829,183.
Notice of allowance dated May 4, 2010 for U.S. Appl. No. 11/468,002.
Office action dated Apr. 4, 2014 for U.S. Appl. No. 12/829,183.
Office action dated May 9, 2012 for U.S. Appl. No. 12/829,183.
Office action dated Sep. 29, 2009 for U.S. Appl. No. 11/468,002.
Office action dated Oct. 20, 2014 for U.S. Appl. No. 12/829,183.
Office action dated Nov. 13, 2012 for U.S. Appl. No. 12/829,183.
Pappone, et al. Cardiac Contractility Modulation by electric currents applied during the refractory period in patients with heart failure secondary to ischemic or idiopathic dilated cardiomyopathy. Am J Cardiol 2002;90(12):1307-1313.
Pappone, et al. First Human Chronic Experience with Cardiac Contractility Modulation by Nonexcitatory Electrical Currents for Treating Systolic Heart Failure: Mid-Term Safety and Efficacy Results from a Multicenter Study. J Cardiovasc Electrophysiol 2004;15:418-427.
Peschar et al., "Left Ventricular Septal and Apex Pacing for Optimal Pump Function in Canine Hearts," J Am Coll Cardiol, 2003;41:1218-26.
Reiter et al.., "Effects of Mechano-Electrical Feedback: Potential Arrhythmogenic Influence in Patients With Congestive Heart Failure," Cardiovascular Research, 1996; 32:44-51.
Smailys et al., "Investigation of the Possibilities of cardiac Defibrillation by Ultrasound," Resuscitation, 1981; 9:233-242.
Sowton, "Clinical Results with the Tachylog Antitachycardia Pacemaker", PACE 1984; 7(Part II):1313-1317.
Stix, et al. Chronic electrical stimulation during the absolute refractory period of the myocardium improves severe heart failure. European Heart J 2004;25:650-655.
Suchkova, et al. Ultrasound improves tissue perfusion in ischemic tissue through a nitric oxide-dependent mechanism. Throm Haemost. 2002;88:865-70.
Tacker. Chapter 1: Fibrillation causes and criteria for defibrillation. In Defibrillation of the Heart. Tacker, WA, ed. Mosby-Year Book, Inc., St. Louis, Missouri, 1994, pp. 1-14.
The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," N Engl J Med. 1997; 337:1576-1583.
Valls-Bertault et al., "Adverse Events with Transvenous Left Ventricular Pacing in Patients with Severe Heart Failure: Early Experience from a Single Centre," Europace, 2001;3:60-63.
Warren et al., "Clinical Evaluation of Automatic Tachycardia Diagnosis by an Implanted Device", PACE 1986;9 (Part II):1079-1083.
Zakharov, et al. The action of Ultrasound on the Contraction Strength and Cation Potential of the Papillary Muscle of the Rat Heart. Biul Eksp Biol Med. Apr. 1989; 107(4):423-6.
Zakharov, et al. The Effect of Acoustic Cavitation on the Contraction Force and Membrane Potential of Rat Papillary Muscle. Ultrasound Med. Biol. 1989; 15 (6):561-5.

\* cited by examiner

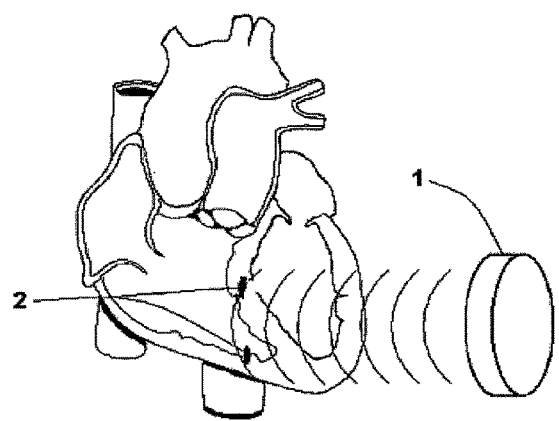
Figure 3b
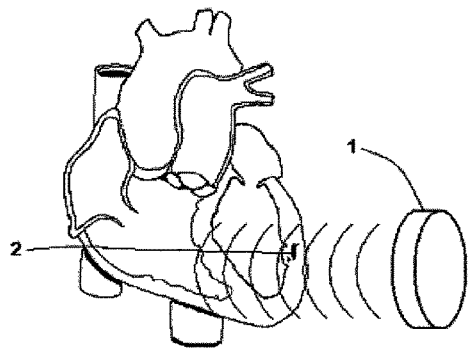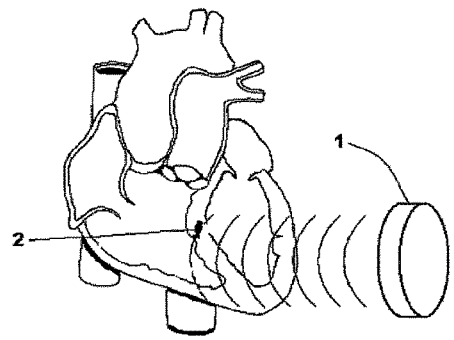
Figure 4a  Figure 4b

METHOD AND SYSTEMS FOR HEART FAILURE PREVENTION AND TREATMENTS USING ULTRASOUND AND LEADLESS IMPLANTABLE DEVICES

CROSS-REFERENCES TO RELATED APPLICATIONS

The present application is a divisional of U.S. patent application Ser. No. 12/829,183, filed Jul. 1, 2010, now U.S. Pat. No. 9,333,364, which is a divisional of U.S. patent application Ser. No. 11/468,002, filed Aug. 29, 2006, now U.S. Pat. No. 7,765,001, which claims the benefit of provisional U.S. Application No. 60/713,241, filed Aug. 31, 2005, the full disclosures of which are incorporated herein by reference.

The disclosure of this application is also related to non-provisional application Ser. No. 11/315,023, filed on Dec. 21, 2005, which claims priority to provisional application 60/689,606 filed on Jun. 9, 2005, and to non-provisional application Ser. No. 10/869,631, filed on Jun. 15, 2004, the full disclosures of which are incorporated herein by reference.

BACKGROUND OF THE INVENTION

Field of the Invention

The methods and systems of this invention relate to the prevention and treatment of heart failure by means of a leadless external or implantable device.

Heart Failure (HF) currently affects over 5 million patients in the United States alone. This population has been steadily increasing due to overall demographic aging and, in particular, the effects of new life-prolonging treatments to patients with chronic cardiac conditions. HF is defined by the ACC/AHA Task Force as a complex clinical syndrome that impairs the ability of the ventricle to fill with or eject blood. HF generally results from one or more underlying factors including hypertension, diabetes, valvular disease, cardiomyopathy, coronary artery disease, or structural changes to the heart muscle. HF is characterized by reduced ventricular wall motion in systole and/or diastole, and low ejection fraction. As the heart becomes less able to pump a sufficient volume of blood to the system, patients develop symptoms of fluid retention, shortness of breath, and fatigue. Patients with cardiac disease or patients who experience cardiac problems, e.g., ischemic episodes, are highly likely to eventually develop HF. It will be beneficial to offer preventative treatment to these patients so that they might avoid or postpone becoming HF patients.

SUMMARY OF THE INVENTION

New medications developed to treat HF have been generally ineffective, and device-based solutions appear to offer significant promise for afflicted patients in both preventing heart failure initially and ameliorating the progression of heart failure. The following are descriptions of four device-based therapies to treat, prevent, and/or delay progression of HF.

First, there are several reports of using therapeutic ultrasound to increase cardiac contractility, reduce aortic pressure, cause coronary vasodilatation, or increase tissue perfusion (tissue sonication). These reports describe the application of continuous and pulsed ultrasound over a wide range of treatment durations, timing intervals, ultrasound frequencies, and ultrasound intensities. In isolated rat papillary muscle, Forester et al. demonstrated increased contractility with continuous wave ultrasound. They speculated that the increase in contractility was due to the thermal effects or mechanical tension effects of ultrasound energy on the sarcolemma (external muscle membrane). Dalecki et al. found that the delivery of pulsed ultrasound to the frog heart in systole resulted in a reduction in the peak aortic pressure. Miyamoto et al. reported vasodilation of coronary arteries in canine studies by short term ultrasound therapy, with the magnitude of the dilation similar to that of intracoronary nitroglycerin. They speculated that the observed coronary vasodilation was a direct effect on vasomotor tone, and reported no temperature change to implicate a thermal effect. Suchkova et al., applied ultrasound to the surface of rabbit limb muscles following arterial ligation, and found that tissue perfusion was increased, accompanied by histologic evidence of dilated capillary beds. They further found this improvement in perfusion to be blocked by inhibition of nitric oxide synthase, implying that the mechanism of effect was dependent upon nitric oxide. Finally, animal studies have shown that ultrasound treatment can cause new myocardial tissue growth in conditions of chronic ischemia, and this is thought to be due to up-regulation of growth factor expression.

Thus, a number of underlying mechanisms have been proposed to explain why therapeutic ultrasound may have beneficial effects on cardiac function. It is possible that increased myocardial contractility, reduced aortic pressure, coronary vasodilation, and increased tissue perfusion occur by separate or related mechanisms. For example, the vasodilation may be secondary to the increased myocardial demand caused by increased contractility. Alternatively, a reduction in aortic pressure (afterload) may result in increased contractility. Increased tissue perfusion may be a manifestation of vasodilation at the capillary level.

While the exact mechanism(s) and sequence of events are not well understood, the beneficial effects of therapeutic ultrasound on cardiac function can be utilized to improve the care of patients with heart failure both chronically and during acute exacerbations. Long term improvement in heart failure treatment is possible with chronic intermittent ultrasound administration. Coronary artery disease is the underlying cause of HF in two-thirds of HF patients and coronary artery disease can lead to acute ischemic episodes, which can be treated by improving blood flow (reperfusion). Since ultrasound therapy can improve blood flow, therapeutic ultrasound can, thus, prevent HF. We have described the use of ultrasound in co-pending application Ser. No. 10/869,631, with methods and systems for leadless implantable devices that directly prevent and/or treat heart failure using ultrasound energy.

Second, the indications for permanent cardiac pacemaker implantation have greatly expanded to include the treatment of heart failure by pacing both the left and right ventricle, called cardiac resynchronization therapy (CRT) or bi-ventricular pacing. Randomized clinical trials have shown significant morbidity and mortality benefits with bi-ventricular pacing, especially when combined with an implantable cardioverter defibrillator (ICD). As described in co-pending application Ser. No. 11/315,023, and Ser. No. 11/315,524, a method of cardiac stimulation uses one or more implantable acoustic receiver-stimulators for cardiac stimulation, along with an implanted or externally-applied ultrasound controller-transmitter. Using this leadless system to avoid lead limitations and complications and gain other potential advantages as described in the co-pending applications, CRT therapy is applied to optimal single or multiple sites in the left or right heart and most notably endocardial left ventricular sites.

Third, another device therapy applying electrical current to the heart muscle is called Cardiac Contractility Modulation (CCM). These systems have some similarities to conventional cardiac pacemakers, in that they comprise a pulse generator implanted in the pectoral region of the chest and transvenous leads having electrodes in direct contact with heart tissue; in some cases, conventional pacemaker leads have been used in CCM therapy. However, in a conventional cardiac pacemaker, electrical current is delivered at sufficient amplitude and duration at a time in the cardiac cycle that will initiate a heart beat, known in the art as excitation. In contrast, for CCM therapy, electrical current is delivered during or immediately after a heart beat when the heart is unable to initiate another beat, known in the art as the absolute refractory period of the heart. The amplitude and duration of the electrical current would be sufficient for excitation, but since it is delivered in this refractory period it is thus considered non-excitatory. Instead of initiating a heat beat via excitation, the electrical field or electrical current delivered for CCM increases tissue contractility during the heart beat. As noted earlier, increased tissue contractility leads to improved cardiac function. It has been shown in basic investigational studies using this CCM approach that the action potential duration is prolonged during this non-excitatory electrical field delivery. It is thought that the underlying mechanism is an increase in calcium transport into the cells.

Early animal studies (Mohri et al.) employed two pairs of electrodes, one pair in the anterior LV wall and one pair in the posterior wall; each with approximately 3 cm interelectrode distance. CCM non-excitatory electrical field delivery (20 mA biphasic square-waves of 30 ms duration) was delivered 30 ms after local R wave detection, between each electrode pair. An increase in contractility was found with either anterior or posterior delivery, but was greatest with simultaneous delivery to both the anterior and posterior pairs. The increase in contractility only occurred in the regions of electrical current delivery.

In acute human studies (Pappone et al.), CCM therapy was delivered either across two selected poles of an octapolar catheter in the coronary sinus (CS), on the epicardial aspect of the LV or on the RV septum from the tip electrode to the ring electrode of a commercially available active fixation pacing lead. The CCM current used was a biphasic, square-wave pulse 20-40 ms in duration, delivered 30-60 ms after detection of an electrical pulse using the local electrogram, with pulse amplitudes up to 14 mA. With LV delivery of 10 mA to the CS, some patients complained of chest discomfort. With RV septum delivery, 14 mA was able to be delivered without chest discomfort. Acute improvement in LV function was similar with LV or RV delivery; approximately a 9% increase in pressure gradient $dP/dt_{max}$ and 10% increase in aortic pulse pressure.

One example of a CCM device is an Optimizer™ II (Impulse Dynamics, Israel). These have been implanted in patients and have been shown to improve cardiac function (Pappone et al., Stix et al.). This device employs one commercially available right atrial lead used for sensing only, and 2 commercially available transvenous bipolar active fixation leads implanted in the RV septum used for sensing a local electrogram and delivery of non-excitatory electrical current.

Because CCM devices use leads similar to cardiac pacemakers, they are subject to all the limitations and complications associated with currently available cardiac pacemakers. These lead issues have been extensively identified in our co-pending applications listed above. Additionally, although animal studies had shown greater efficacy with placement of the electrodes on the left ventricle, in clinical studies using coronary sinus leads for left ventricular non-excitatory CCM therapy, patients experienced chest pain, attributed to stimulation of the phrenic nerve. In the same patients, endocardial delivery to the right ventricular septum did not cause discomfort. It is likely, based on animal study results, that CCM therapy would be substantially improved using a system that enables endocardial left ventricular non-excitatory therapy.

Therefore, it would be desirable to provide a system without the need for transvenous leads, with the ability to optimally select sites on the endocardium, particularly in the left ventricle, and to select multiple sites for CCM delivery of non-excitatory electrical current.

Fourth, the concept of selective site pacing to initiate a preferred pattern of cardiac activation and/or mechanical contraction has been recently put forth to prevent heart failure in patients needing permanent pacing for bradycardia indications. Traditionally, the standard ventricular site for stimulation has been the RV apex for reasons of lead stability and ease of implantation. However, recent randomized clinical trials of patients requiring bradycardia pacing (DAVID and PAVE) have lead to the conclusion that the RV apex location is deleterious. The concept of selective site pacing has emerged, and has led to the reevaluation of all traditional pacing sites. New stimulation sites being evaluated require the use of non-passive fixation tips and more precise implant techniques. The ideal site(s) may be within the left ventricle in areas inaccessible using transvenous leads from within the coronary sinus. Selective site left ventricular or right ventricular stimulation alone may provide improved heart functioning or prevention of heart failure without the need for bi-ventricular stimulation. It would be desirable to provide selective site pacing with previously referred to leadless methods and systems using one or more implantable acoustic receiver-stimulators for cardiac stimulation, along with an implanted or externally-applied ultrasound controller-transmitter. The receiver-stimulator would be implanted in the left and/or right ventricle at one or more locations that initiate a preferred pattern of cardiac activation and/or mechanical contraction.

It would be desirable to treat patients who have had cardiac problems to prevent or delay them from becoming HF patients. It would be ideal to provide a single system to take advantage of the benefits of sonification, pacing and CCM and either based on user preference, pre-programmed therapy, or physiologic parameters that are measured, individual or combination treatments (sonication, pacing or CCM) could be provided.

Thus, it would further be desirable to provide an implantable device that combines the beneficial effects of direct application of ultrasound energy to cardiac tissue with the beneficial effects of a leadless electrical delivery device for cardiac resynchronization stimulation therapy, cardiac contractility modulation therapy, and/or selective site pacing therapy in order to improve cardiac function in heart failure patients or to prevent heart failure in other patients.

2. Description of the Background Art

U.S. Pat. No. 4,651,716 Forester; George V. et al. Method and device for enhancement of cardiac contractility; U.S. Pat. No. 6,522,926 Kieval, et al.; Devices and methods for cardiovascular reflex control; U.S. Pat. No. 3,659,615, Enger; Encapsulated Non-Permeable Piezoelectric Powered Pacesetter, 5/1972. U.S. Pat. No. 4,256,115, Bilitch; Leadless Cardiac Pacer, 3/1981; U.S. Pat. No. 4,690,144, Rise et al; Wireless Transcutaneous Electrical Tissue Stimulator, 9/1987; U.S. Pat. No. 5,170,784, Ramon et al; Leadless Magnetic Cardiac Pacemaker, 12/1992; German Patent DE4330680 (abandoned), Zwicker; Device for Electrical Stimulation of Cells within a Living Human or Animal, 3/1995; U.S. Pat. No. 5,405,367, Schulman et al; Structure and Method of Manufacture of an Implantable Microstimulator, 4/1995; U.S. Pat. No. 5,411,535, Fujii et al; Cardiac Pacemaker Using Wireless Transmission, 155/1995; U.S. Pat. No. 5,749,909, Schroeppel et al; Transcutaneous Energy Coupling Using Piezoelectric Device, 5/1998; U.S. Pat. No. 5,751,539, Stevenson et al; EMI Filter for Human Implantable Heart Defibrillators and Pacemakers, 5/1998; U.S. Pat. No. 5,766,227, Nappholz et al; EMI Detection in an Implantable Pacemaker and the like, 5/1998; U.S. Pat. No. 5,814,089, Stokes et al; Leadless Multisite Implantable Stimulus and Diagnostic System, 9/1998; U.S. Pat. No. 5,817,130, Cox et al; Implantable Cardiac Cardioverter/Defibrillator with EMI Suppression Filter with Independent Ground Connection, 10/1998; U.S. Pat. No. 5,978,204, Stevenson; Capacitor with Dual Element Electrode Plates, 11/1999; U.S. Pat. No. 6,037,704, Welle; Ultrasonic Power Communication System, 3/2000; U.S. Pat. No. 6,366,816, Marchesi; Electronic Stimulation Equipment with Wireless Satellite Units, 4/2002; U.S. Patent Application Publication 2002/0077673, Penner et al; Systems and Methods for Communicating with Implantable Devices, 6/2002; U.S. Pat. No. 6,424,234, Stevenson; Electromagnetic Interference (EMI) Filter and Process for Providing Electromagnetic Compatibility of an Electronic Device while in the Presence of an Electromagnetic Emitter Operating at the Same Frequency, 7/2002; U.S. Pat. No. 6,445,953, Bulkes et al; Wireless Cardiac Pacing System with Vascular Electrode-Stents, 9/2002; U.S. Pat. No. 6,654,638, Sweeney; Ultrasonically Activated Electrodes, 11/2003; U.S. Patent Application Publication 2004/0172083, Penner; Acoustically Powered Implantable Stimulating Device, 9/2004; WO9725098, Shlomo et al; Electrical Muscle Controller, 7/1997; U.S. Pat. No. 6,725,093, Ben-Haim et al; Regulation of excitable tissue control of the heart based on physiological input, 4/2004; U.S. Pat. No. 6,463,324, Ben-Haim et al; Cardiac output enhanced pacemaker, 10/2002; U.S. Pat. No. 6,442,424, Ben-Haim et al. Local cardiac motion control using applied electrical signals, 8/2002; U.S. Pat. No. 6,363,279, Ben-Haim et al; Electrical muscle controller, 3/2002; U.S. Pat. No. 6,330,476, Ben-Haim et al; Electrical muscle controller using a non-excitatory electric field, 12/2001; U.S. Pat. No. 6,317,631, Ben-Haim et al; Controlling heart performance using a non-excitatory electric field, 11/2001; U.S. Pat. No. 6,298,268, Ben-Haim et al; Cardiac output controller, 10/2001; U.S. Pat. No. 6,285,906, Ben-Haim et al; Muscle contraction assist device, 9/2001; U.S. Pat. No. 6,236,887, Ben-Haim et al; Drug-device combination for controlling the contractility of muscles, 5/2001; U.S. Pat. No. 6,233,484, Ben-Haim et al; Apparatus and method for controlling the contractility of muscles, 5/2001; ACC/AHA Task Force on Practice Guidelines. Evaluation and Management of Chronic Heart Failure in the Adult. JACC 2002; 38:2101-13; Miyamoto T et al. Coronary Vasodilation by Noninvasive Transcutaneous Ultrasound An In Vivo Canine Study. Journal of the American College of Cardiology. 2003; 41:1623-7; McPherson D and Holland C. Seizing the Science of Ultrasound Beyond Imaging and Into Physiology and Therapeutics. Journal of the American College of Cardiology 2003; 41:1628-30; Forester G V, Roy O Z, and Mortimer A J. Enhancement of contractility in rat isolated papillary muscle with therapeutic ultrasound. Mol. Cell Cardiol. 1982; 14(8):475-7; Suchkova V N, et al. Ultrasound improves tissue perfusion in ischemic tissue through a nitric oxide-dependent mechanism. Throm Haemost. 2002; 88:865-70; Dalecki D. et al. Effects of pulsed ultrasound on the frog heart: I. Thresholds for changes in cardiac rhythm and aortic pressure. Ultrasound in Med & Biol. 1993; 19:385-390; Mortimer A J et al. Letter to the Editor: Altered Myocardial Contractility with Pulsed Ultrasound. Ultrasound in Med and Biol. 1987; 13(9):L567-9; Forester G V et al. Ultrasound Intensity and Contractile Characteristics of Rat Isolated Papillary Muscle. Ultrasound in Med. And Biol. 1985; 11(4):591-598; Meltzer R S, Schwarz K Q, et al. Therapeutic Cardiac Ultrasound. American Journal of Cardiology. 1991; 67:422-4; Kass D A, Chen C-H, Curry C, Talbot M, Berger R, Fetics B, Nevo E. Improved Left Ventricular Mechanics from Acute VDD Pacing in Patients with Dilated Cardiomyopathy and Ventricular Conduction Delay. Circulation 1999; 99:1567-73; Abraham W T, Fisher W G, Smith A L, Delurgio D B, Leon A R, Loh E, Kocovic D Z, Packer M, Clavell A L, Hayes D L, Ellestad M, Messenger J, for the MIRACLE study group; Cardiac Resynchronization in Chronic Heart Failure. N Engl J Med, 2002; 346:1845-53; Nishida T, et al. Extracorporeal cardiac shock wave therapy markedly ameliorates ischemia-induced myocardial dysfunction in pigs in vivo. Circulation. 2004; 110:3055-3061; Mohri S, et al. Cardiac contractility modulation by electric currents applied during the refractory period. Am J Physiol Heart Circ Physiol. 2002; 282:H1642-1647; Marrouche N F et al. Nonexcitatory stimulus delivery improves left ventricular function in hearts with left bundle branch block. J Cardiovasc Electrophysiol. 2002; 13:691-695; Mond H G, Gammage M D. Selective Site Pacing: The Future of Cardiac Pacing? PACE 2004; 27:835-836; Peschar M, et al. Left ventricular septal and apex pacing for optimal pump function in canine hearts. J Am Coll Cardiol 2003; 41:1218-1226; DAVID Trial Investigators. The Dual Chamber and VVI Implantable Defibrillator (DAVID) Trial. JAMA 2002; 288:3115-3123; Doshi, R N, et al. The Left Ventricular-Based Cardiac Stimulation Post AV Nodal Ablation Evaluation (PAVE) Study, oral presentation at American College of Cardiology, March 2004; Pappone C, et al. Cardiac Contractility Modulation by electric currents applied during the refractory period in patients with heart failure secondary to ischemic or idiopathic dilated cardiomyopathy. Am J Cardiol 2002; 90:1307-1313; Pappone C, et al. First human chronic experience with cardiac contractility modulation by nonexcitatory electrical currents for treating systolic heart failure: mid-term safety and efficacy results from a multicenter study. J Cardiovasc Electrophysiol 2004; 15:418-427; Stix G, et al. Chronic electrical stimulation during the absolute refractory period of the myocardium improves severe heart failure. European Heart J 2004; 25:650-655.

BRIEF SUMMARY OF THE INVENTION

The devices of the present invention deliver ultrasound energy to the heart and/or deliver ultrasound energy to receiver-stimulator devices. Delivered at therapeutic levels, the ultrasound energy directly improves cardiac function by increasing contractility, vasodilation, and tissue perfusion, etc. This leads to prevention of HF in patients who are likely to become HF patients, if left untreated, and in patents who are already diagnosed with HF. Delivered at sufficient amplitudes, the ultrasound energy is transduced into electrical energy by implanted receiver-stimulator devices that have been implanted in the heart tissue, providing either excitatory or non-excitatory energy delivery for the treatment of heart failure. In combination, ultrasound therapy and receiver-stimulator device therapy provide multiple benefits as heart failure therapies, including preventing patients from degenerating into HF. The use of ultrasound as the single energy source provides efficient selection of individual and combined therapies, as well as tissues sites, for delivering the therapy.

The present invention relies on acoustic energy delivery using an external or implantable device to provide beneficial effects for patients with heart failure including 1) the ability to improve cardiac function from the exposure of acoustic energy to cardiac tissue, and/or 2) the ability to transmit acoustic energy to implanted receivers to provide excitatory and non-excitatory stimulation, in patients suffering from or at risk of heart failure.

We have previously disclosed methods and systems to treat heart failure by means of a leadless implantable device delivering vibrational (ultrasound, acoustic) energy from a controller-transmitter device to directly improve cardiac function. We have also previously disclosed methods and devices of leadless implantable systems for the electrical stimulation of cardiac tissue using ultrasound as a means to transmit energy and signal information from a controller-transmitter device throughout the body to one or more receiver-stimulator devices containing means to receive such ultrasound, convert it into electrical energy, and then apply that electrical energy to stimulating electrodes as cardiac resynchronization therapy for the treatment of heart failure. See co-pending application Ser. No. 11/315,023, filed Dec. 21, 2005; Ser. No. 11/315,524, filed Dec. 21, 2005; and patent application Ser. No. 10/869,631, filed Jun. 15, 2004, the full disclosures of which are incorporated here by reference.

In all these co-pending applications, acoustic energy is applied from an external or implanted controller-transmitter to the heart tissue to provide at least one of an increase in contractility, vasodilation, tissue perfusion, and/or an increase in cardiac output for the treatment of heart failure.

In some of these co-pending applications, acoustic energy is applied from an external or implanted controller-transmitter to implanted receiver-stimulator devices in the heart to provide electrical delivery for bi-ventricular pacing or selective site pacing.

It is an intent of this invention to provide methods and systems for the leadless electrical delivery of non-excitatory therapy in cardiac contractility modulation for the treatment of heart failure. It is a further intent of this invention to provide methods and systems for the leadless electrical delivery of excitatory therapy for the prevention of heart failure. It is still a further intent of this invention to provide methods and systems to select and deliver separate heart failure treatment and preventive therapies within a single system. It is yet another intent of this invention to provide methods and systems to combine and deliver in a single system multiple heart failure treatment and preventive therapies to yield multiple therapeutic benefits.

External or implanted controller-transmitters according to the present invention are configured to apply acoustic energy to at least a portion of the heart, usually including at least a ventricular region(s) of the heart and typically including regions of the heart with implanted receiver-stimulator devices.

A controller-transmitter device may be implanted utilizing known surgical techniques subcutaneously, above or beneath the pectoral muscles, near the heart. This device will typically contain some, most, or all elements of currently available pacemaker systems, with specific adaptations pertinent to this invention. Such typical elements may include a power source, such as a battery or a rechargeable battery; logic control and timing circuitry; a sensing system, typically comprising sensing electrodes, motion detectors, and other types of physiologic sensors; signal conditioning and analysis functions for the various electrodes and detectors; and a system to communicate with an outside console for data transmission, diagnostic, and programming functions typically through a radiofrequency (RF) link. Additionally, the controller-transmitter device usually contains an ultrasound amplifier and an ultrasound transducer to generate acoustic energy, and to transmit such energy in the general direction of the heart and specifically in the direction of the implanted receiver-stimulator device. Beam profiles of the transmitted acoustic energy may be adapted to target portions of the heart or implanted receiver-stimulator devices. The duration, timing, and power of the acoustic energy transmission would be controlled as required, in response to detected natural or induced physiological events or conditions, and per programmed parameters of the device, by the logic control electronics.

In order to provide excitatory or non-excitatory electrical delivery to cardiac tissue employing ultrasonic energy transfer, the present invention comprises an implantable receiver-stimulator device adapted to be implanted at or attached to the desired location either endocardially, epicardially, or intramyocardially. Various techniques and tools (catheters, stylets) that are commonly known could be used to implant the receiver-stimulator device at these locations. The receiver-stimulator would be adapted to provide permanent attachment at the implant site including possibly helical coils, barbs, tines, clips, or the like, or by bonding onto its outer surface materials which are known to stimulate cellular growth and adhesion. Alternatively, the receiver-stimulator could be adapted for implantation in the coronary vasculature at preferred sites for stimulation, e.g., being incorporated into a stent-like platform suitable for intravascular delivery and deployment. Functionally, the receiver-stimulator device comprises 1) an ultrasound transducer to receive the acoustic energy transmitted from a controller-transmitter device and transform it into electrical energy, 2) an electrical circuit to transform the alternating electrical energy into a direct current or a waveform having other characteristics (e.g., multiphase waveforms), and 3) electrodes to transfer the electrical energy to the myocardium.

A single receiver-stimulator device may be implanted as described above for single site excitatory or non-excitatory electrical delivery to cardiac tissue. Alternatively, a plurality of receiver-stimulator devices could be implanted to deliver excitatory or non-excitatory electrical energy to cardiac tissue, either by simultaneous, sequential or independent activation of the receiver-stimulator devices. The transmitted acoustic energy can activate the stimulators simultaneously or sequentially through fixed or programmable delays after receiving the same transmitted acoustic energy, or independently by responding only to acoustic energy of a specific character (i.e., of a certain frequency, amplitude, or by other modulation or encoding of the acoustic waveform) intended to energize only that specific device.

In one embodiment, a controller-transmitter would contain programmable parameter settings to activate receiver-stimulators that have been implanted at critical sites to deliver leadless non-excitatory CCM therapy to improve cardiac function of heart failure patients. A plurality of receiver-transmitters would be implanted into the left and/or right heart at selected locations in order to provide a non-excitatory electrical field. The controller-transmitter would include sensing electrodes on, connected to, or incorporated into its external surface and signal processing circuitry and algorithms to allow it to detect the patient's electrogram (electrocardiographic recording). Signal processing and specialized algorithms would recognize intrinsic atrial and/or ventricular activation and possibly also electrocardiographic indices of action potential duration such as the QT interval. Following a detected intrinsic ventricular activation and a programmed delay interval, the controller-transmitter would then activate the receiver-stimulator devices at energy levels that are therapeutic.

In another embodiment, a controller-transmitter would contain programmable parameters to activate receiver-stimulators that have been implanted at critical sites to deliver excitatory (pacing) therapy to prevent heart failure.

In yet another embodiment, a controller-transmitter would contain programmable parameter settings to provide direct therapeutic sonication of ventricular tissue, and contain programmable parameters to activate receiver-stimulators to deliver leadless bi-ventricular pacing therapy or site selected pacing therapy for heart failure, and contain programmable parameters to activate receiver-stimulators that have been implanted at critical sites to deliver pacing therapy as a prevention of heart failure, and contain programmable parameters to activate receiver-stimulators that have been adapted and implanted in critical sites to deliver CCM therapy to improve the tissue condition of heart failure patients.

In another preferred embodiment, a controller-transmitter would contain programmable parameters settings to deliver combinations of therapy for direct therapeutic sonication of ventricular tissue, leadless bi-ventricular or critical site pacing, heart failure prevention pacing, and/or CCM therapy. In such an embodiment one or more receiver-stimulator elements adapted for its specific function would necessarily be implanted at desired locations within the heart, preferably fully embedded within the myocardium. The specialized controller-transmitter would then be implanted subcutaneously at a location allowing sonication of tissue in both ventricles and activation of one or more implanted receiver-stimulators. Any of the therapies described could be used independently or in combination to accomplish multi-beneficial therapy. The controller-transmitter would include sensing electrodes on or incorporated into its external surface and signal processing circuitry and algorithms to allow it to detect physiologic parameters (e.g. electrograms, pacing artifact signals from an implanted conventional pacemaker, pressure, heart sounds, motion/activity, etc.) to allow algorithmic adjustment to one or more therapies.

BRIEF DESCRIPTION OF THE DRAWINGS

FIG. 3b illustrates a system for performing CCM therapy directly on cardiac tissue.

FIGS. 4a-4d illustrate different implantation sites for the receiver-stimulator.

DETAILED DESCRIPTION OF THE INVENTION

The present invention relies on a controller-transmitter device to deliver ultrasound energy to cardiac tissue to directly improve cardiac function and/or to energize one or more implanted receiver-stimulator devices that transduce the ultrasound energy to electrical energy to perform excitatory and/or non-excitatory treatments for heart failure. The acoustic energy can be applied as a single burst or as multiple bursts with appropriate selection of the following parameters:

| Parameter | Value Range |
| --- | --- |
| Ultrasound frequency | 20 kHz-5 MHz |
| Ultrasound Burst Duration | 0.1 [LS-100 mS |
| Duty Cycle | 0.001-6.0% |
| Mechanical Index | <1.9 |

Figure 1:
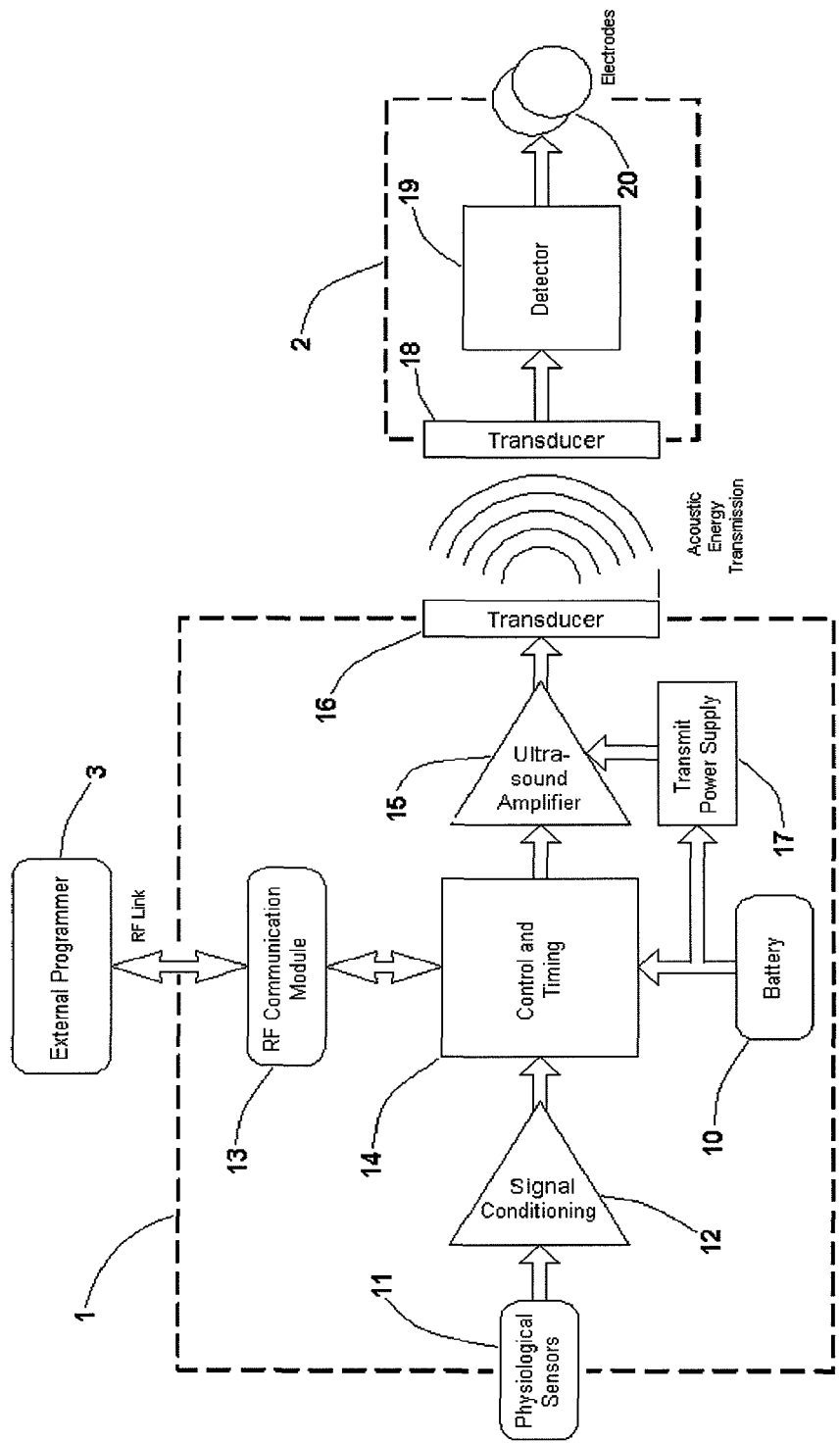
FIG. 1 is a block diagram of the components of a system constructed according to the principles of the present invention.

FIG. 1 is a block diagram of the present invention. An implantable controller-transmitter device 1 contains an ultrasound transducer 16 (or multiple transducers) of appropriate size(s) and aperture(s) to generate sufficient acoustic power to achieve the desired heart failure therapy. The transducer(s) 16 within the controller-transmitter device 1 are constructed of specific designs, including aperture size, acoustic frequency, materials, and arrangement to provide the appropriate beam characteristics for individual embodiments, implant sites, and patient characteristics. The controller-transmitter 1 contains the power source, typically a battery 10, ultrasound amplifier 15, transmission power conditioning 17, control and timing electronics and logic 14, physiologic sensor interface electronics 12, sensors 11 either encapsulated in the device or connected to the device, and a communication module 13 typically an RF communication interface to an external control and programming device 3. An external controller-transmitter would contain the same elements, except the external programmer 3 and RF communication module 13. The external controller-transmitter would have an operator-controlled interface (not shown) to adjust device parameters.

The transducer(s) 16 may comprise a single element or several elements in a linear, two-dimensional, or segmented array (not shown). In the case of an array, each element may have its own amplifier 15 and control and timing electronics and logic 14 such that the acoustic beam might be focused or diffused depending on the desired function or effect, or steered to a desired location, or that the beam may be swept to cover several sites in sequential order, or any combination thereof.

The one or more receiver-stimulator implants 2 contain a receiver transducer 18, circuitry 19 to detect, impedance match, and convert the received ultrasound energy into an electrical output, and electrodes 20. Multiple receiver-stimulator devices 2 may function simultaneously; it is also possible for multiple devices to function sequentially by incorporating different delays within the circuitry 19, or independently, either by responding only to a specific transmitted frequency by steering the transmit beam to specific devices, or through the use of a selective modulation technique such as amplitude modulation, frequency modulation, pulse width modulation, or through encoding techniques including time-division multiplexing, which would be discriminated by adapting circuitry 19.

Figure 2:
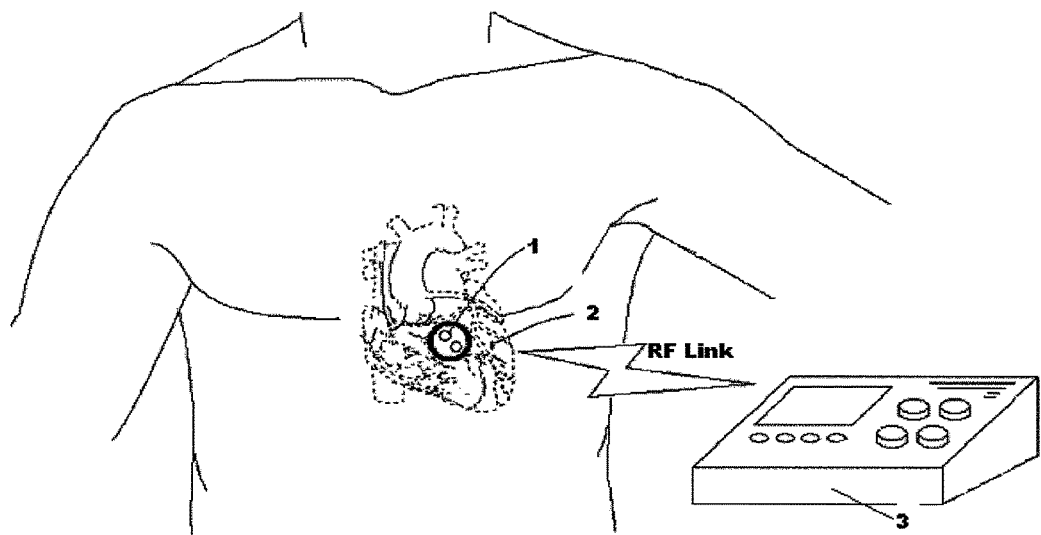
FIG. 2 illustrates a controller-transmitter implanted over a patient's heart and in communication with a receiver-stimulator and an external programmer.

FIG. 2 illustrates the functional components of the present invention for an implanted embodiment. The controller-transmitter device 1 containing the transmitting transducer 5 would be implanted typically just beneath the skin in the subcutaneous space but could also be placed beneath the pectoral muscles. In particular, it is desirable to be able to direct the ultrasonic energy over the left ventricle in order to assure maximum effectiveness. As the heart is located beneath the ribs and sternum, the controller-transmitter device 1 must be properly located to deliver the energy. At frequencies lower than 1 MHz, acoustic attenuation due to bone and cartilage is less problematic.

The receiver-stimulator device(s) 2 would be implanted typically using an endocardial placement technique by an active fixation mechanism such as a helical screw-in element. Alternatively the receiver-stimulator device(s) 2 could be implanted using a minimally invasive surgical approach to the epicardial aspects of the heart or delivered transvascularly into, for example, the coronary sinus. Locations for the receiver-stimulator devices would be chosen to optimize the desired electrical therapy.

The controller-transmitter device 1 would typically include physiological sensors 11 (not shown) such as electrodes disposed on the outer surface of the device, for detecting the patient's electrogram, and in certain embodiments additional physiological sensors including but not limited to sensors which would detect the patient's motion, blood pressure, respiration, and/or heart sounds. Circuitry and algorithm logic 14 for utilizing these signals for control of the devices' therapeutic function could be incorporated in the system. Such electrodes and other sensors would be preferably disposed on or incorporated into or within the housing of the controller-transmitter device.

An external programmer 3 is used to program device parameters in the controller-transmitter 1, typically using an RF telemetry link. Programming of the controller-transmitter includes the selection of one or more of the following types of therapies: (i) Sonication of heart tissue to improve cardiac function; (ii) Site-selected pacing for prevention of heart failure; (iii) Multi-site pacing (e.g. bi-ventricular pacing) for treatment of heart failure; and (iv) Cardiac Contractility Modulation to improve contractility.

Alternatively, the acoustic transmitter function for direct therapeutic sonication of heart tissue might also be incorporated within a device delivering conventional lead-based electrical current (not shown), for example, within a CRT device or within a CCM device wherein the conventional lead/electrode system would provide sensing from and electrical delivery to cardiac tissue and the acoustic transmission would provide ultrasound therapy for heart failure.

Figure 3A:
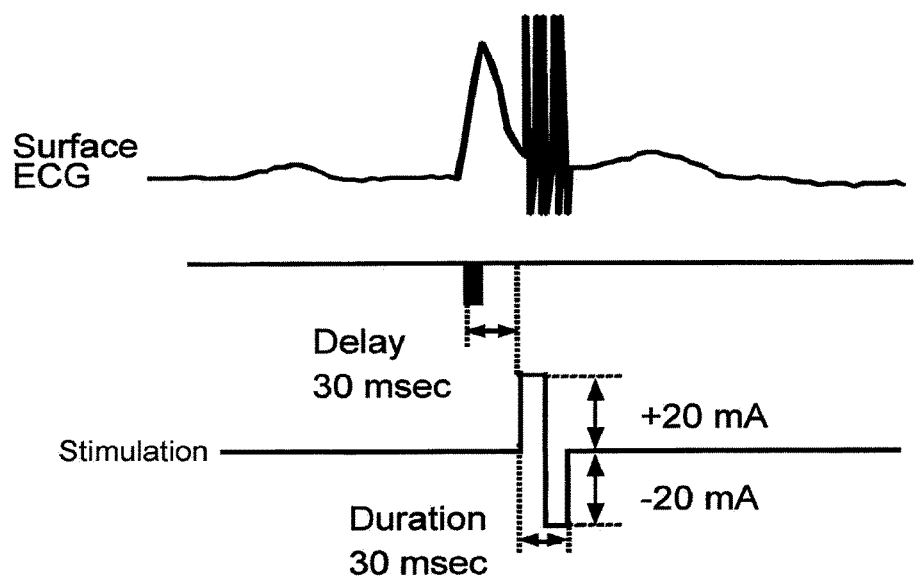
FIG. 3a illustrates prior art timing parameters.

FIG. 3a, shown adapted from prior art (Mohri), is an example to illustrate the types of timing needed within for the control circuitry 14 to perform CCM therapy using the present invention. Sensing electrodes on a controller-transmitter device 1 provide a signal similar to the surface ECG shown in the diagram. The onset of electrical ventricular activation is detected, and after a specified delay (here shown as 30 msec), the transmitter delivers acoustic energy for a specified duration which is transduced by circuitry 19 into an appropriate electrical waveform. The duration of the electrical delivery (here shown as 30 msec) is equal to the duration of acoustic delivery. In this example, the electrical waveform is biphasic (positive square wave followed by negative square wave) with an amplitude of 20 mA, but other waveforms may be used.

FIG. 3b shows a preferred embodiment for a system combining direct acoustic therapy to the cardiac tissue with CCM therapy. In FIG. 3b, two receiver-stimulator devices 2 are implanted into the right ventricle, one in the septum and the other at the apex. Other implant locations in the right and left ventricle may be selected for any number of receiver-stimulators 2. Inherent ventricular activation is detected from sensing electrodes incorporated on the controller-transmitter 1 whereby the control circuitry properly times the initiation of the delivery of acoustic energy to the two implanted receiver-stimulators 2 to initiate non-excitatory therapy.

Figure 4C:
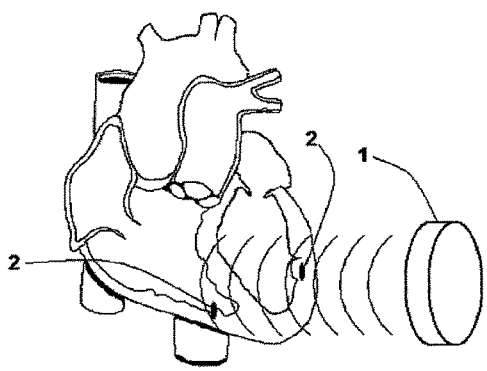

FIGS. 4a-4d depict various illustrations of receiver-stimulator implant site selections. FIG. 4a is a cross-sectional view of the heart showing a single receiver-stimulator device 2 implanted into the left ventricular myocardium. Such an embodiment may be functional for site specific pacing for the prevention of heart failure in a patient needing bradycardia pacing support, for site specific pacing for the treatment of heart failure, or for CCM therapy to improve cardiac contractility in a heart failure patient. As shown, with appropriate placement of the controller-transmitter 1, both the cardiac tissue and the receiver-stimulator 2 will receive ultrasound waves thus providing an opportunity for sonication therapy in a heart failure patient.

FIG. 4b is a cross-sectional view of the heart showing a single receiver-stimulator 2 implanted into the ventricular septum, receiving acoustic energy from controller-transmitter 1. Similarly, such an embodiment may be functional for site specific pacing for the prevention of heart failure in a patient needing bradycardia pacing support or for CCM therapy delivery to improve the wall motion characteristics of the septum in a patient with HF.

FIG. 4c shows a further adaptation wherein two receiver-stimulator devices 2 are implanted to achieve a completely leadless multi-site pacemaker configuration for example as in bi-ventricular pacing or a multi-site CCM therapy delivery for HF treatment. The first receiver-stimulator 2 is shown attached to the right ventricular apex with the second being attached to the left ventricular free wall. Both receiver-stimulator devices 2 and the ventricles receive acoustic energy from controller-transmitter 1 simultaneously. Direct beneficial sonication therapy may be delivered to the ventricles. Excitatory (pacing) and non-excitatory (CCM) therapy may be delivered either simultaneously or selectively.

Figure 4D:
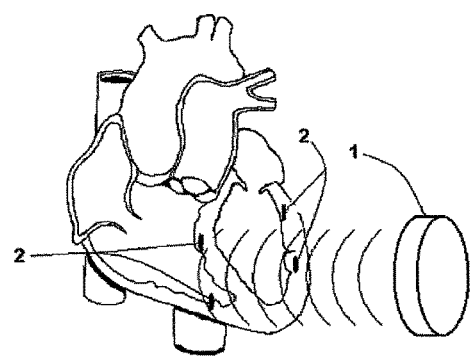

FIG. 4d shows another alternative embodiment. In this example, four receiver-stimulator devices 2 are implanted into the right and left ventricle and can be used for multiple therapy concepts. As in FIG. 4c, since the ultrasound is delivered to the cardiac tissue and receiver-stimulators simultaneously, direct beneficial sonication therapy may be delivered simultaneously. Excitatory (pacing) and non-excitatory (CCM) therapy may be delivered either simultaneously or selectively.

Optionally, but not shown, a receiver-stimulator 2 could also be implanted into the atrial tissues of the heart. Optionally, but not shown, this multi-therapy concept could integrate the ultrasound sonication therapy with a conventional dual chamber pacemaker (DDD), dual chamber ICD, bi-ventricular pacemaker (CRT-P), biventricular pacemaker ICD (CRT-D), or a CCM therapy device.

Optionally, the invention can provide three types of heart failure treatments to the patient either separately or in combination; direct sonication of the ventricular tissue, cardiac contractility modulation therapy, and excitatory pacing stimulation.

What is claimed is:

1. A system for heart failure therapy comprising:
one or more acoustic receiver-stimulators having an electrode assembly comprising electrodes adapted to be implanted in direct contact with cardiac tissue at one or more heart locations selected to provide a preferred pattern of activation and/or mechanical contraction; and
an acoustic controller-transmitter comprising a housing and at least one physiological sensor disposed on an outer surface of the housing, wherein the controller-transmitter and receiver-stimulator are adapted to transmit and receive acoustic energy which provides both energy and signal information to the receiver-stimulator sufficient to stimulate the heart, wherein the receiver-stimulator comprises an acoustic receiver which receives acoustic energy and generates alternating current and converter circuitry which produces a direct current or waveform from the alternating current to stimulate the cardiac tissue; and wherein at least one of the electrodes is adapted to deliver the direct current or waveform to myocardial tissue;
wherein the acoustic controller-transmitter is adapted to transmit the acoustic energy to provide two or more of the following functions: (a) direct therapeutic ultrasound sonication of heart tissue to improve cardiac function or prevent deterioration of cardiac function, (b) leadless pacing to improve cardiac function or prevent deterioration of cardiac function, and (c) leadless cardiac contractility modulation to improve cardiac function or prevent deterioration of cardiac function; wherein cardiac function is one or more of contractility, vasodilation, tissue perfusion, or aortic pressure; wherein cardiac function is one or more of contractility, vasodilation, tissue perfusion, or aortic pressure.

2. A system as in claim 1, wherein the implantable receiver-stimulator is adapted to be placed and secured at a location in the right ventricle.

3. A system as in claim 2, wherein the implantable receiver-stimulator is adapted to be placed and secured at the ventricular septum.

4. A system as in claim 1, wherein the controller-transmitter is external.

5. A system for the delivery of therapy to a patient's heart, comprising:
one or more acoustic receiver-stimulators having an electrode assembly adapted to be implanted in direct contact with the heart; and
an acoustic controller-transmitter, wherein the controller-transmitter is adapted to transmit acoustic energy into the patient's body to provide two or more of the following functions:
(a) direct therapeutic ultrasound sonication of heart tissue to improve cardiac function or prevent deterioration of cardiac function, (b) leadless pacing to improve cardiac function or prevent deterioration of cardiac function, and (c) leadless cardiac contractility modulation to improve cardiac function or prevent deterioration of cardiac function;
wherein cardiac function is one or more of contractility, vasodilation, tissue perfusion, or aortic pressure.

6. A system as in claim 5, wherein leadless pacing or leadless cardiac contractility modulation therapy is delivered by the one or more acoustic receiver-stimulators and activated by the said acoustic controller-transmitter;
wherein the controller-transmitter and receiver-stimulator are adapted to transmit and receive acoustic energy which provides both energy and signal information to the receiver-stimulator;
wherein the receiver-stimulator comprises an acoustic receiver which receives acoustic energy and generates alternating current, and means for converting the alternating current to a direct current or waveform to electrodes adapted to deliver the direct current or waveform to myocardial tissue;
wherein the controller-transmitter directs acoustic energy to the receiver-stimulator;
wherein the implantable receiver-stimulator is adapted to be placed and secured at a location sufficient to prevent and/or treat heart failure; and
wherein the controller-transmitter is external.

* * * * *